United States Patent [19]
Haber et al.

[11] Patent Number: 5,707,365
[45] Date of Patent: Jan. 13, 1998

[54] INSULIN DISPENSER

[75] Inventors: Terry M. Haber, El Toro; William H. Smedley, Lake Elsinore; Clark B. Foster, Laguna Niguel, all of Calif.

[73] Assignee: Eli Lilly and Company, Indianapolis, Ind.

[21] Appl. No.: 692,596

[22] Filed: Aug. 6, 1996

[51] Int. Cl.$^6$ ................................................ A61M 5/00
[52] U.S. Cl. ............................................ 604/191; 604/89
[58] Field of Search ................................ 604/191, 187, 604/83–90, 247, 248, 218, 204, 205, 249

[56] References Cited

U.S. PATENT DOCUMENTS 5,286,258  2/1994  Haber et al. ................. 604/191 X

*Primary Examiner*—John D. Yasko
*Attorney, Agent, or Firm*—Morland C. Fischer

[57] ABSTRACT

An insulin dispenser having a retractable needle cannula and an easy to transport and store disk-shaped body. First and second plungers are removably received in first and second plunger storage chambers that extend through the body. First and second fluid medications are stored in first and second fluid storage chambers that extend through the body. A fluid accumulator having an accumulator plunger moveable therethrough lies in fluid communication with the first and second fluid storage chambers. The first and second plungers are first removed from the first and second plunger storage chambers to be located in and moved through the first and second fluid storage chambers to cause the first and second fluid medications therein to be expulsed to and combined within the fluid accumulator. The accumulator plunger is then moved through the fluid accumulator to cause the combined first and second fluid medications to be injected to a diabetic via the needle cannula.

20 Claims, 4 Drawing Sheets

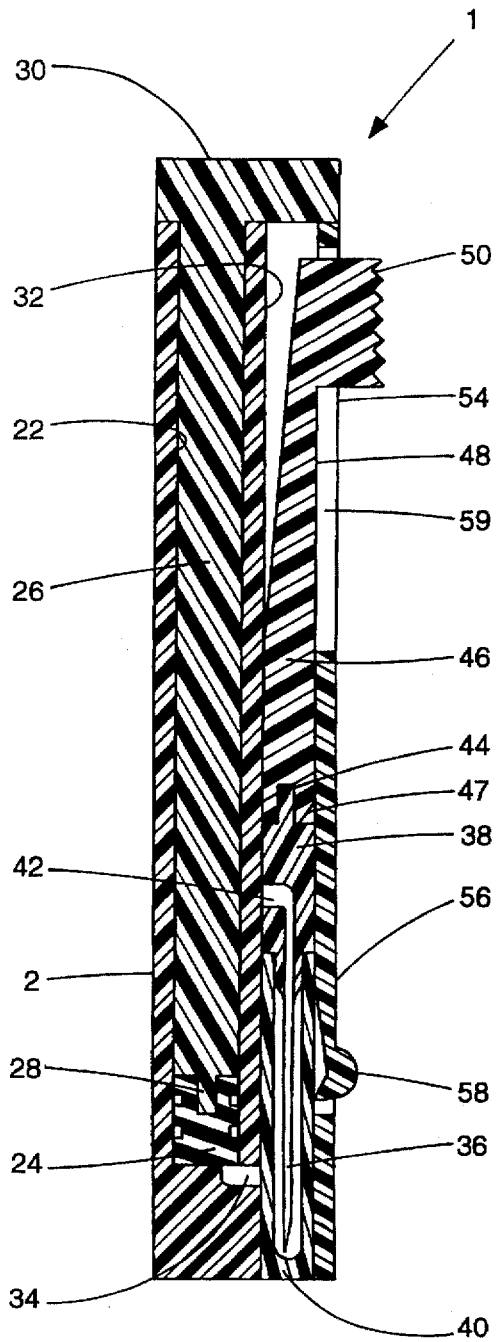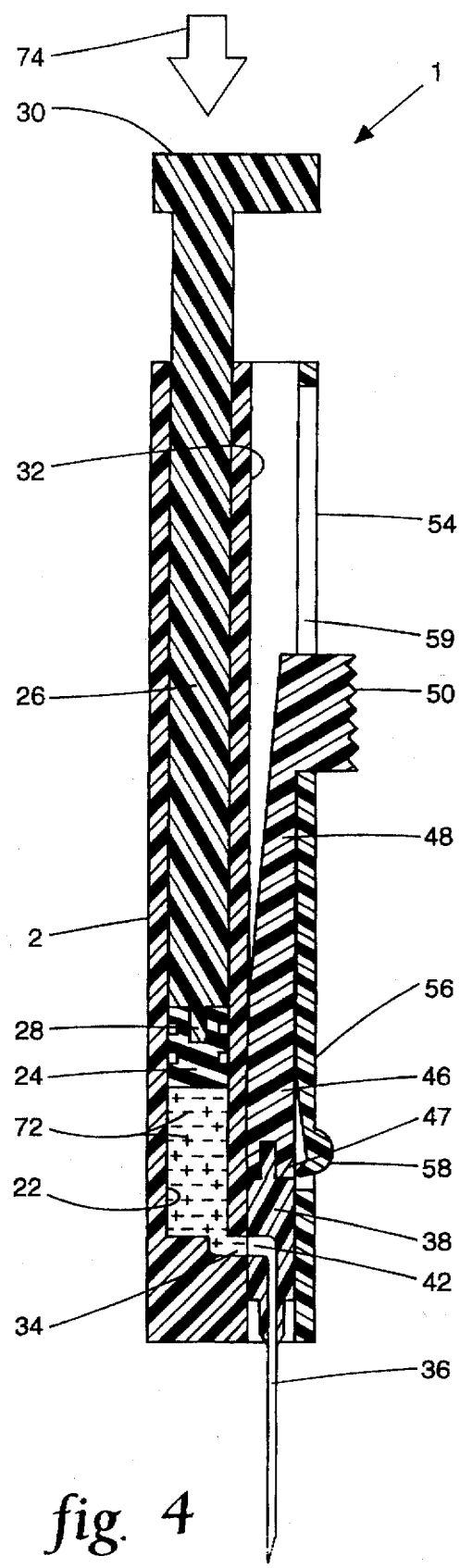
fig. 3
fig. 4

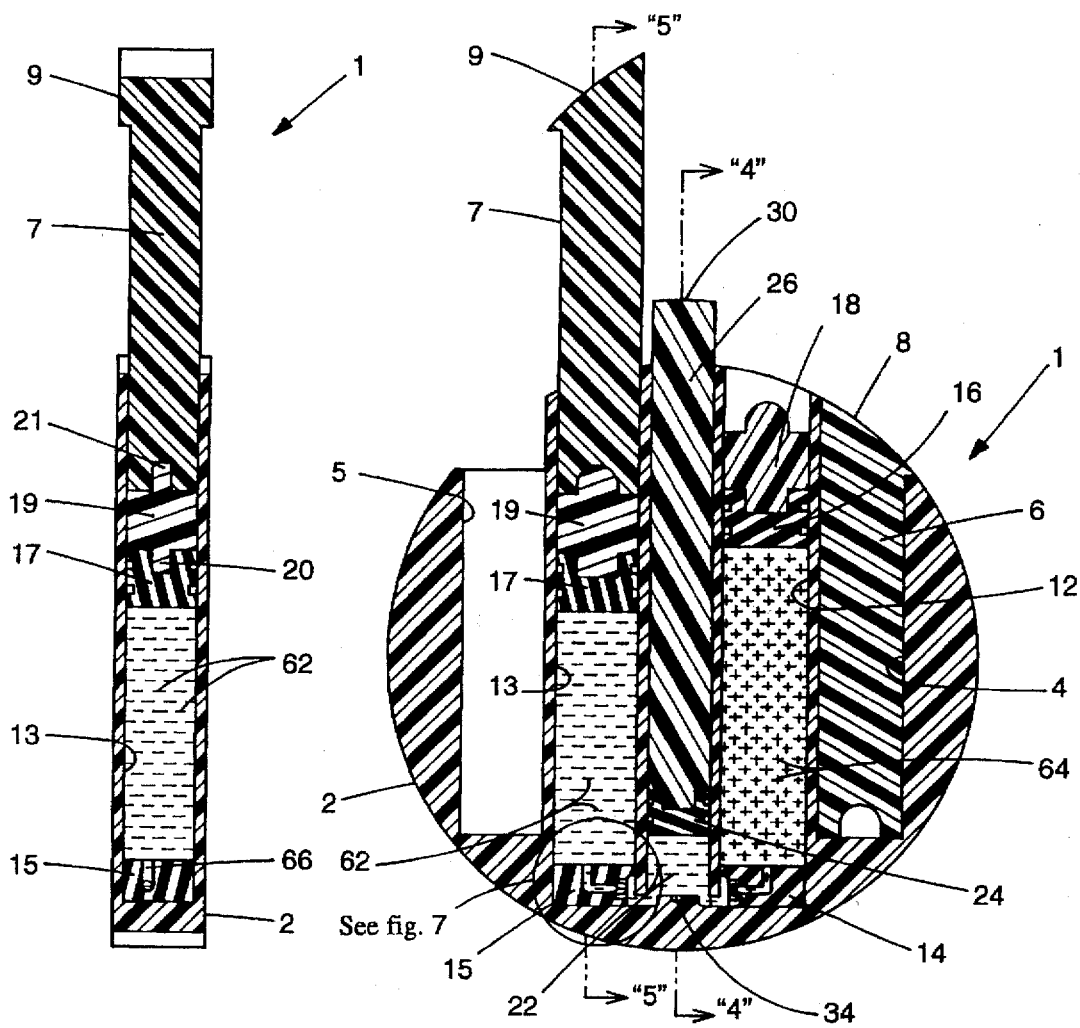
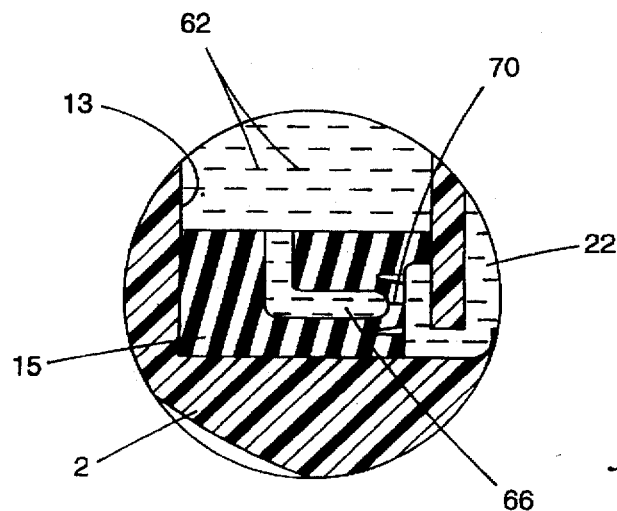
fig. 5
fig. 6
fig. 7

INSULIN DISPENSER

BACKGROUND OF THE INVENTION

1. Field of the Invention

This invention relates to an insulin dispenser having a retractable needle cannula and a compact and aesthetically pleasing housing in which first and second fluid medications are stored and combined with one another to produce an insulin solution to be injected to a diabetic.

2. Background Art

A diabetic is typically required to inject himself several times a day with two different types of insulin (e.g. types N and R) to enable him to withstand the physical effects caused by diabetes. A diabetic may wish to adjust the volume of types N and R insulin to be injected depending upon his daily schedule so as to take into account eating, sleeping, physical activity, and the like, as well as the rates at which the types of insulin will react with his body. Being able to administer frequent injections and tightly controlled levels of types N and R insulin relatively to one another are known to dramatically reduce bodily distress brought on by diabetes.

Traditionally, the diabetic must give himself a series of two injections by first removing the different types of insulin from two medication vials. Thus, the diabetic is required to carry on his person the medication vials as well as one or more syringes to administer the insulin injections. The foregoing is inconvenient, cumbersome and often subjects the diabetic to embarrassment as a consequence of having to carry and use a variety of drug delivery paraphernalia. That is to say, besides suffering from diabetes in and of itself, the diabetic is also left with the uncomfortable feeling that casual observers may consider him to be a drug abuser. Moreover, the sight of a diabetic using such drug delivery paraphernalia, alone, may be enough to scare away would-be friends and/or associates.

It would therefore be desirable to enable diabetics to have a single, compact and non-threatening (i.e. aesthetically pleasing) insulin dispenser in which to store and combine two different fluid medications for injection so as to reduce the stigma that is frequently associated with treating diabetes.

SUMMARY OF THE INVENTION

In general terms, an insulin dispenser is disclosed having an efficient and aesthetically pleasing disk-like main body, the size and shape of which resembles a lady's compact. A series of parallel aligned chambers run through the main body. A pair of plunger storage chambers receive therewithin a respective pair of plungers. A pair of fluid storage chambers are filled with first and second fluid medications that are to be combined to form an insulin solution for injection to a diabetic. The fluid storage chambers are closed to the atmosphere by pistons located at the proximal end of each chamber. A normally closed, one way fluid check valve is located at the distal end of each fluid storage chamber. A centrally disposed fluid accumulator extends diametrically through the main body of the insulin dispenser. The fluid accumulator is initially devoid of fluid. However, an accumulator plunger and an associated piston are located within and moveable through the fluid accumulator.

An elongated recess or guide track is formed in the main body of the insulin dispenser so as to lie above the fluid accumulator. A fluid transfer port is formed through the guide track to communicate with the fluid accumulator thereunder. A needle hub having a hypodermic needle cannula projecting therefrom and a fluid aperture communicating with the cannula is located within and moveable along the guide track of the main body. A needle control arm having a textured finger grip is located within the guide track and coupled to the needle hub so that an axial pushing force applied to the needle control arm at the finger grip thereof is transferred to the needle hub to cause the hub and the needle cannula carried thereby to be advanced through the guide track to extend outwardly from the main body when an insulin injection is to be administered. The guide track is closed by a cover plate which fits over top the needle hub and the needle control arm. A needle position control slot extends longitudinally through the cover plate for receipt of the finger grip of the needle control arm. The finger grip is adapted to ride through the needle position control slot when the needle cannula that is carried by the needle hub is advanced outwardly of the main body so that the injection can be administered.

In operation, the plungers are removed from their plunger storage chambers and relocated to respective fluid storage chambers to be coupled to the pistons at the proximal ends of the fluid storage chambers. Each plunger is pushed distally through its fluid storage chamber to drive the coupled piston towards a check valve. The first and second fluid medications stored in the fluid chambers are now compressed, whereby to cause the check valves to momentarily open so that predetermined volumes of the first and second fluid medications are expulsed to and combined with one another within the fluid accumulator. The needle cannula is then advanced axially through the guide track and outwardly of the main body by the user applying a distal pushing force against the needle control arm, which pushing force is transferred to the needle hub. The movement of the needle hub through the guide track completes a fluid path between the fluid accumulator and the needle cannula via the fluid transfer port through the guide track and the fluid aperture in the needle hub. Finally, the accumulator plunger is pushed distally to drive the coupled piston through the fluid accumulator and thereby cause the insulin solution consisting of a mixture of the first and second fluid medications to be expulsed through the needle cannula by way of the aforementioned fluid path. Accordingly, the injection is completed at which time the needle carrying hub may be replaced by a new hub to be retracted with its cannula inwardly of the main body of the insulin dispenser to await the next injection.

A BRIEF DESCRIPTION OF THE DRAWINGS

FIG. 3 is a cross-section of the insulin dispenser in an at-rest condition;

FIG. 4 is a cross-section taken along lines 4—4 of FIG. 6 showing the insulin dispenser in an active condition at which to administer an insulin injection;

FIG. 5 is a cross-section taken along lines 5—5 of FIG. 6;

FIG. 6 is a cross-section of the insulin dispenser in the active condition; and

FIG. 7 is an enlarged detail of a one-way, normally closed check valve taken from FIG. 6.

DETAILED DESCRIPTION

Figure 1:
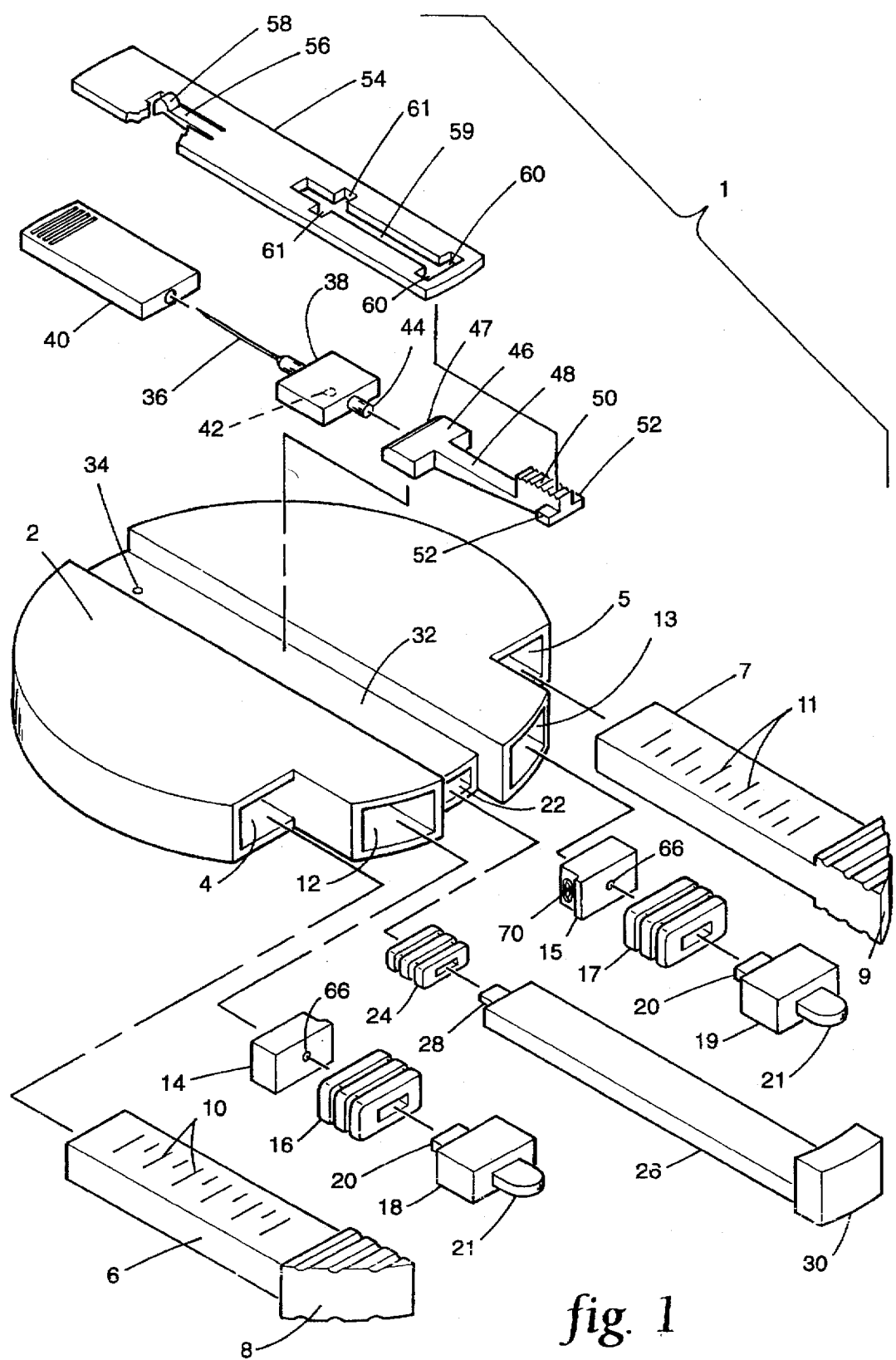
FIG. 1 is an exploded view of the insulin dispenser which forms the present invention.
Figure 2:
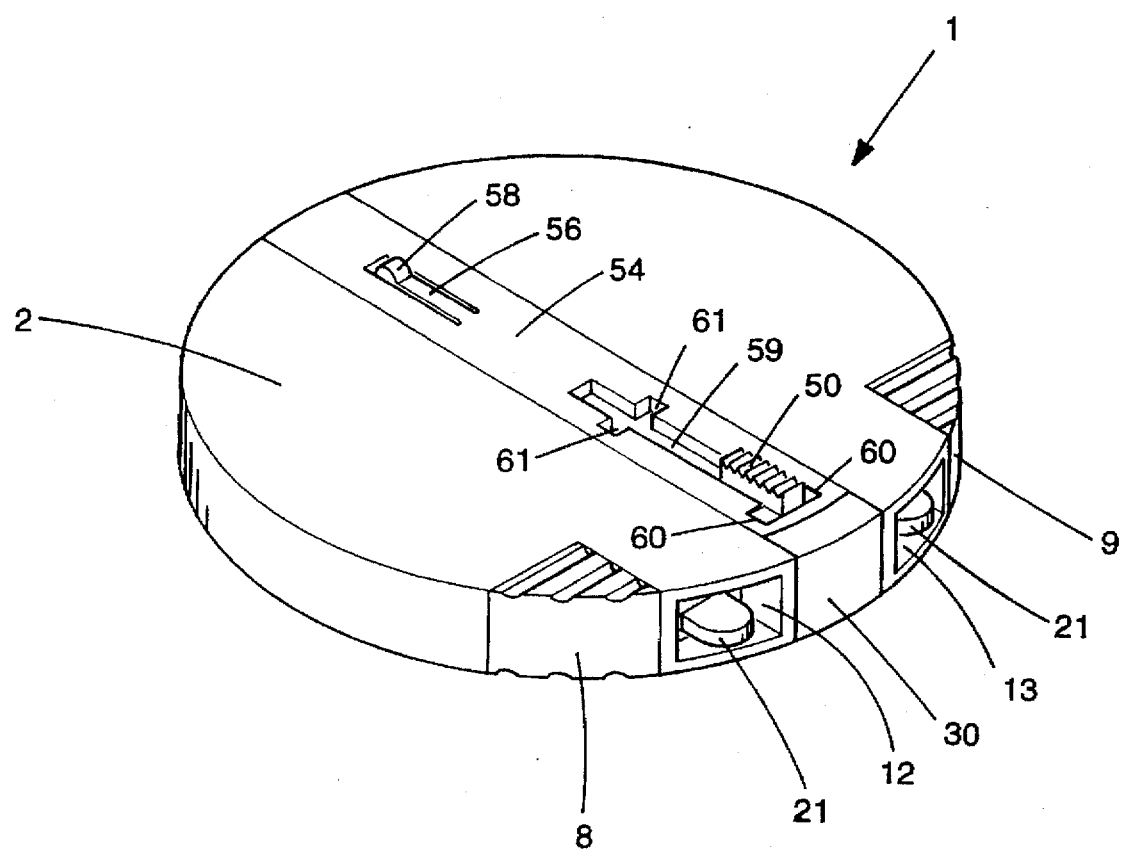
FIG. 2 shows the insulin dispenser of FIG.1 in the assembled configuration.

The insulin dispenser 1 which forms the present invention is now described while referring initially to FIG. 1 and 2 of the drawings. Insulin dispenser 1 has a disk-like main body 2. The main body 2 is specifically shaped to have the size and appearance of a lady's compact in order to be convenient to carry and store and, more importantly, to improve the cosmetic appearance of the insulin dispenser 1 so as not to attract the attention of passers-by and thereby reduce some of the stigma and self-consciousness that might otherwise be suffered by a diabetic who could be perceived by some as a drug abuser.

The main body 2 of insulin dispenser 1 has a series of parallel aligned chambers running therethrough. An outermost pair of plunger storage chambers 4 and 5 of main body 2 are sized to accommodate therewithin a respective pair of plungers 6 and 7.

Each plunger 6 and 7 has an elongated plunger body projecting from a relatively wide plunger head 8 and 9. The plunger heads 8 and 9 have textured gripping surfaces to allow the plungers 6 and 7 to be grasped and manipulated relative to their storage chambers 4 and 5 and soon to be described fluid storage chambers 12 and 13. The bodies of the plungers 6 and 7 have sets of calibration lines 10 and 11 to enable the insulin dispensing process to be selectively and accurately controlled.

An inner pair of fluid storage chambers 12 and 13 of main body 2 are disposed between the outer pair of plunger storage chambers 4 and 5 and a central fluid accumulator 22. As will be described in greater detail hereinafter, in the at-rest condition of the insulin dispenser 1, the plungers 6 and 7 are initially located in respective plunger storage chambers 4 and 5, and the fluid storage chambers 12 and 13 are filled with different fluid medications that are to be combined and delivered to the user during the administration of an insulin injection.

One-way, normally closed check valves 14 and 15 are located at the distal end of each of the fluid storage chambers 12 and 13 in which a fluid medication is carried (best shown in FIG. 5–7). The proximal end of each fluid storage chamber 12 and 13 is closed to the atmosphere by means of an elastomeric piston 16 and 17 followed by a rigid piston support 18 and 19. The piston supports 18 and 19 have opposing tabs 20 and 21 projecting therefrom by which to engage and couple the plungers 6 and 7 to respective pistons 16 and 17 after the plungers 6 and 7 have been removed from their plunger storage chambers 4 and 5 for insertion within and movement through fluid storage chambers 12 and 13 during the administration of an injection of insulin with the insulin dispenser i in an active condition. In this manner, a sliding movement of the plungers 6 and 7 through fluid storage chambers 12 and 13 is transferred to the pistons 16 and 17 to cause a corresponding movement of pistons 16 and 17 towards check valves 14 and 15.

A centrally disposed fluid accumulator 22 extends diametrically through the main body 2 of insulin dispenser 1 between the inner pair of fluid storage chambers 12 and 13. In the at-rest condition of insulin dispenser 1, an elastomeric piston 24 followed by an accumulator plunger 26 are located within and completely fill the fluid accumulator 22. The accumulator plunger 26 has a tab 28 projecting from the distal end thereof by which to couple the plunger 26 to the piston 24 so that a sliding movement of the accumulator plunger 26 through the fluid accumulator 22 causes a corresponding movement of the piston. The distal end of the accumulator plunger 26 has a relatively wide head 30 which will become manually accessible so that a pushing force can be applied thereto to cause the accumulator piston 24 to slide through the fluid accumulator 22 during the administration of an insulin injection when insulin dispenser 1 is in the active condition.

The fluid accumulator 22 is relatively narrow compared with the plunger storage chambers 4 and 5 and the fluid storage chambers 12 and 13. In this same regard, the accumulator plunger 26 is thinner than the plungers 6 and 7 so as to be accommodated by the relatively narrow fluid accumulator 22. As a result of the foregoing, a guide track 32 (i.e. an elongated recess) runs along the main body 2 of insulin dispenser 1 over the fluid accumulator 22. A fluid transfer port 34 extends through the distal end of the guide track 32 so as to lie in fluid communication with the fluid accumulator 22 thereunder for an important purpose that will soon be disclosed.

A single ended hypodermic needle cannula 36 is carried by and projects from the distal end of a generally flat needle hub 38. In the at-rest condition of the insulin dispenser 1, the needle cannula 36 is covered by a removable needle sheath 40 to preserve the sterility of the cannula and prevent an accidental needle stick. A fluid aperture 42 (shown in phantom lines in FIG. 1) is located at the bottom of the needle hub 38 to supply fluid to cannula 36. When the insulin dispenser 1 is in the active condition, the fluid aperture 42 through needle hub 38 can be moved with the hub 38 to be placed in fluid communication with the fluid transfer port 34 through guide track 32 so as to establish a fluid path between the fluid accumulator 22 and the needle cannula 36.

The needle hub 38 is coupled to a reaction block 46 at the distal end of a needle control arm 48 by means of a post 44 projecting from the proximal end of hub 38 for receipt by a receptacle (not shown) in the reaction block 46. The face 47 of reaction block 46 is sloped for a purpose that will soon be described. A textured finger grip 50 is located at the proximal end of needle control arm 48 so that an axial force applied at the finger grip 50 of needle control arm 48 will be transferred to the needle hub 38 to cause a corresponding displacement of the needle cannula 36. A pair of stops 52 projects outwardly from opposites sides of the finger grip 50 of needle control arm 48 so as to lock the control arm 48 and the needle hub 38 coupled thereto in either advanced or retracted positions relative to the main body 2 of insulin dispenser 1.

At the distal end of a latch cover plate 54 is a flexible latch arm 56. The latch arm carries a detent 58 which projects below the latch cover plate 54. A longitudinally extending needle position control slot 59 is formed through the proximal end of latch cover plate 54. A pair of relatively wide notches 60 and 61 is formed at the opposite ends of the needle position control slot 59.

The latch cover plate 54 is sized and shaped to conform to the guide track 32 that runs along the top of the main body 2 of insulin dispenser 1. In the assembled configuration of FIG. 2, the latch cover plate 54 is mated to the needle control arm 48 so that the position of the needle cannula 36 carried by needle hub 38 relative to the main body 2 can be controlled. More particularly, the needle control arm 48, the needle carrying hub 38 and the needle sheath 40 are all located within and moveable through the guide track 32 atop the fluid accumulator 22. The latch cover plate 54 is then coupled to the needle control arm 48 to cover the guide track 32 such that the finger grip 50 of control arm 48 is received in and adapted to ride through the needle position control slot 59 of plate 54. Opposite sides of the latch cover plate 54 are affixed (e.g. adhesively bonded) to the main body 2 so as to close the guide track 32 and thereby prevent the inadvertent removal of the needle hub 38 and the needle control arm 48.

In the at-rest condition of insulin dispenser 1, the stops 52 of finger grip 50 are located within respective notches 60 at the proximal end of the needle position control slot 59 through latch cover plate 54 so as to lock the position of needle control arm 48 at a retracted position within the guide track 32 and thereby prevent the premature displacement of needle cannula 36 outwardly of the main body 2 prior to the time that an insulin injection is to be administered.

The operation of the insulin dispenser 1 is now disclosed in the at-rest condition (best shown in FIGS. 2 and 3 of the drawings). The plungers 6 and 7 are first located within their respective plunger storage chambers 4 and 5 so that insulin dispenser 1 may be conveniently transported or stored. At the same time, the fluid storage chambers 12 and 13, which are filled with first and second fluid medications (designated 62 and 64 in FIG. 6) that are to be combined in and injected to the diabetic user from the fluid accumulator 22, are sealed by the respective coupled connections of pistons 16 and 17 to piston supports 18 and 19, such that the tabs 21 of piston supports 18 and 19 are accessible at the proximal ends of each fluid storage chamber 12 and 13. The fluid accumulator 22, within which the first and second fluid medications of fluid storage chambers 12 and 13 are to be supplied for injection, is initially devoid of any fluid. In this case, the interconnection of piston 24 and accumulator plunger 26 are located completely through the fluid accumulator 22, such that plunger head 30 closes the proximal end of accumulator 22.

In the at-rest condition of insulin dispenser 1, the needle cannula 36 and the needle sheath 40 are retained in a retracted position relative to the main body 2. That is, and as is best shown in FIG. 3, the textured finger grip 50 of needle control arm 48 is located and locked at the proximal end of the needle position control slot 59 of latch cover plate 54 by means of the stops 52 of needle control arm 48 being received by the proximal notches 60 of needle position control slot 59. Therefore, the needle cannula 36 and the needle sheath 40 are correspondingly retained inwardly of the main body 2 of insulin dispenser 1 prior to the injection. Accordingly, it may be appreciated that in the at-rest condition of the insulin dispenser 1 shown in FIG. 2, nothing projects outwardly from the disk-like main body 2 so as to advantageously create a fully self-contained, extremely efficient and aesthetically pleasing package that is convenient to transport and store away.

The insulin dispenser 1 is manipulated in the active condition when it is desirable to administer an injection of insulin to the diabetic user. In this case, the different fluid medications located within the fluid storage chambers 4 and 5 are combined within and expulsed from the fluid accumulator 22. To accomplish the foregoing, and referring now to FIGS. 4-7 of the drawings, the plungers 6 and 7 are removed, one at a time, from their respective plunger storage chambers 4 and 5 and relocated to the fluid storage chambers 12 and 13. Each plunger 6 and 7 is coupled to its rigid support block 18 and 19 by means of the tabs 21, while each of the support blocks 18 and 19 is connected to its elastomeric piston 16 and 17 by means of tabs 20.

With the plunger head (e.g. designated 9 at FIGS. 5 and 6) of one of the plungers (e.g. 7) now projecting outwardly from its fluid storage chamber (e.g. 13), the user applies an inward pushing force against plunger head 9. The inward pushing force is transferred to the associated piston 17 via plunger 7 and piston support 19, whereupon piston 17 will slide distally through fluid storage chamber 13 towards the check valve 15 located at the distal end of chamber 13. Accordingly, a hydraulic pressure builds up in response to the first fluid medication 62 being compressed within fluid storage chamber 13, whereby the first fluid medication 62 will be expulsed from fluid storage chamber 13 to fluid accumulator 22 via check valve 15.

The volume of fluid medication 62 expulsed from fluid storage chamber 13 to fluid accumulator 22 can be selectively controlled by the diabetic user. Since about a one week supply of insulin is preferably carried by the insulin dispenser 1, the user will typically not wish to inject the complete contents of fluid storage chambers 12 and 13 during any one injection. In this regard, the calibration lines (designated 10 and 11 in FIG. 1) on the plungers 6 and 7 help the user identify the distance to be covered by plunger 7 moving through chamber 13 so as to cause a precise volume of fluid medication to be expulsed that is required to serve the user's particular medical needs.

Turning briefly to FIG. 7 of the drawings, the check valve 15 between fluid storage chamber 13 and fluid accumulator 22 is now disclosed. It is to be understood that check valve 15 is identical to the check valve 14 between fluid storage chamber 12 and fluid accumulator 22. Check valve 15 has an elastomeric (e.g. rubber) body that is adapted for one-way fluid flow (i.e. fluid cannot be returned from accumulator 22 to storage chamber 13 via check valve 15). A fluid passage 66 is formed through the body of check valve 15. The fluid passage 66 communicates with fluid storage chamber 13 and terminates at a slit 70 that is normally closed to the flow therepast of fluid (i.e. fluid medication 62). The normally closed slit 70 extends between fluid passage 66 and fluid accumulator 22.

When the insulin dispenser 1 is at rest and the plunger 7 is located in its plunger storage chamber 5, the slit 70 will remain closed, whereby the flow of fluid medication 62 from fluid chamber 13 to fluid accumulator 22 will be blocked. When the plunger 7 is removed from its plunger storage chamber 5 and moved distally through storage chamber 13 to simultaneously cause piston 17 to slide towards check valve 15, the hydraulic pressure created when the fluid medication 62 is compressed is transmitted to slit 70. Hence, slit 70 will be momentarily opened to permit the fluid medication 62 to be expulsed, under pressure, to fluid accumulator 22 by way of fluid passage 66 and the now open slit 70. Once the movement of plunger 7 and piston 17 through fluid storage chamber 13 is discontinued, the slit 70 will automatically return to its at-rest closed condition to once again block fluid communication between fluid storage chamber 13 and fluid accumulator 22.

After a suitable volume of the first fluid medication 62 has been expulsed to the fluid accumulator 22, the second plunger 6 is removed from its plunger storage chamber 4 and moved distally through fluid storage chamber 12 to drive piston 16 towards check valve 14 at the distal end of fluid storage chamber 12. Thus, a precise volume of the second fluid medication 64 will be expulsed from fluid storage chamber 12 to fluid accumulator 22 via one-way check valve 14 in the same manner that was just described with regard to expulsing the first fluid medication 62 to accumulator 22. Accordingly, predetermined volumes of the first and second fluid medications 62 and 64 carried in respective fluid storage chambers 12 and 13 are mixed together in the fluid accumulator 22 so that a combined insulin solution can now be delivered to the diabetic user during the administration of an injection.

During each occasion that the first and second fluid medications 62 and 64 are supplied to the fluid accumulator 22, the fluid volume of the initially fluid free accumulator 22 is increased. Such increase in fluid volume causes the accumulator plunger 26 and the piston 24 coupled thereto to be pushed proximally through the accumulator 22 (as illustrated in FIG. 6). At this point, the accumulator plunger 26 is disposed outwardly of the main body 2 so as to be easily accessible to the user.

In order to administer the insulin injection, and referring specifically to FIG. 4 of the drawings, the user places his thumb on the textured finger grip 50 of needle control arm 48 and applies a downward pushing force thereagainst to move the stops 52 out of the notches 60 at the proximal end of needle position control slot 59. At the same time, the user applies a distal pushing force against the finger grip 50 in order to cause the finger grip to ride axially through the needle position control slot 59 and thereby relocate the needle control arm 48 distally along the guide track 32 in the main body 2 of insulin dispenser 1. The distal relocation of needle control arm 48 causes a corresponding distal relocation of needle hub 38 and the needle cannula 36 carried thereby. Eventually, the needle 36 and the needle sheath 40 are pushed outwardly from the main body 2. Similarly, the stops 52 of needle control arm 48 are now received by and locked within respective notches 61 at the distal end of needle position control slot 59.

It may be appreciated that with the needle cannula advanced and locked outwardly of main body 2, the fluid aperture 42 at the underside of the needle hub 38 is moved into alignment with the fluid transfer port 34 that extends through the distal end of guide track 32 to communicate with fluid accumulator 22. What is more, the distal relocation of needle control arm 48 along guide track 32 also moves the detent 58 which extends from the latch arm 56 below latch cover plate 54 to a position immediately above the gap formed between the sloped face 47 of reaction block 46 and the needle hub 38. Once the needle sheath 40 is removed to expose the needle cannula 36, the insulin dispenser 1 is ready to administer an injection of insulin to the diabetic user.

To complete the injection, and continuing to refer to FIG. 4, the needle cannula 36 first makes a veni puncture through the user's tissue. Next, the user applies a distal pushing force (in the direction of reference arrow 74) to the plunger head 30 of accumulator plunger 26. The distal pushing force is transferred to the piston 24 via the accumulator plunger 26 to correspondingly drive piston 24 distally through the fluid accumulator 22 which now contains an insulin solution 72 consisting of the combination of the first and second fluid medications 62 and 64. The continued distal movement of piston 24 compresses the insulin solution 72 such that the solution is injected, under pressure, from fluid accumulator 22 into the tissue of the diabetic user by way of a fluid path including the fluid transfer port 34 through guide track 32, the fluid aperture 42 in needle hub 38, and the needle cannula 36.

At the conclusion of the injection, the needle hub 38 which carries the needle cannula 36 is typically removed and discarded and a new needle hub may be substituted therefor. To facilitate the detachment of the needle hub 38 from the reaction block 46 of needle control arm 48, the user pushes downwardly on the detent 58 so as to cause the flexible latch arm 56 to rotate below latch cover plate 54. The detent 58 is now wedged into the gap between the sloped face 47 of reaction block 46 and the needle hub 38 so as to detach hub 38 from needle control arm 48. At this point, the user may simply and easily remove the needle hub 38 for a safe disposal.

Once a new needle carrying hub 38 is coupled to needle control arm 48, the new needle cannula thereof may be retracted inwardly of main body 2 to await the next insulin injection. The foregoing is accomplished by the user pushing downwardly on the textured finger grip 50 of needle control arm 48 so as to move the stops 52 out of the notches 61 at the distal end of needle position control slot 59. The user then applies a proximal pushing force to finger grip 50 so as to relocate needle control are 48 and the new needle hub coupled thereto proximally through the guide track 32 and inwardly of main body 2 so as to return the needle cannula to its at-rest condition below the latch cover plate 54.

It will be apparent that while a preferred embodiment of the invention has been shown and described, various modifications and changes may be made without deporting from the true spirit and scope of the invention. For example, although the dispenser 1 has been described above as combining first and second fluid medications to form an insulin solution to be injected to a diabetic user, it is to be understood that dispenser 1 can also be used to store and combine any other two fluids that must be mixed together immediately prior to the administration of an injection. The foregoing may occur when the combination of fluid medications has a short life span or has reduced efficacy after exposure to the atmosphere.

Having thus set forth the preferred embodiment, what is claimed is:

1. A fluid medication dispenser, comprising:

a housing;

first and second fluid storage chambers extending within said housing;

first and second fluid medications located within respective ones of said first and second fluid storage chambers;

a fluid accumulator extending within said housing;

valve means by which to place said first and second fluid storage chambers in fluid communication with said fluid accumulator;

first and second plungers adapted to be positioned within and moved through respective ones of said first and second fluid storage chambers to cause at least some of said first and second fluid medications to be delivered from said first and second fluid storage chambers to said fluid accumulator via said valve means;

first and second plunger storage chambers extending through said housing for removably receiving and storing respective ones of said first and second plungers, said first and second plungers being removed from said first and second plunger storage chambers to be positioned within and moved through respective ones of said first and second fluid storage chambers;

a hypodermic needle adapted to be placed in fluid communication with said fluid accumulator for injecting said first and second fluid medications delivered to said fluid accumulator into living tissue; and means by which to cause said first and second fluid medications to be supplied from said fluid accumulator to said hypodermic needle.

2. The fluid medication dispenser recited in claim 1, wherein said housing is disk-shaped.

3. The fluid medication dispenser recited in claim 1, further comprising first and second pistons located within respective ones of said first and second fluid storage chambers, said first and second pistons being coupled to respective ones of said first and second plungers to be driven through said first and second fluid storage chambers when said first and second plungers move through said first and second fluid storage chambers.

4. The fluid medication dispenser recited in claim 1, wherein said valve means are first and second check valves that are closed to block the delivery of said first and second fluid medications from said first and second fluid storage chambers to said fluid accumulator, said first and second check valves being momentarily opened to permit the delivery of said first and second fluid medications from said first and second fluid storage chambers to said fluid accumulator when said first and second plungers move through said first and second fluid storage chambers.

5. The fluid medication dispenser recited in claim 4, wherein said first and second check valves are located within respective ones of said first and second fluid storage chambers.

6. The fluid medication dispenser recited in claim 1, wherein said means by which to cause said first and second fluid medications to be supplied from said fluid accumulator to said hypodermic needle is an accumulator plunger positioned within and moveable through said fluid accumulator.

7. The fluid medication dispenser recited in claim 6, further comprising an accumulator piston located within said fluid accumulator and coupled to said accumulator plunger to be driven through said fluid accumulator when said accumulator plunger moves through said fluid accumulator.

8. The fluid medication dispenser recited in claim 1, further comprising a fluid transfer port formed through said housing and extending between said fluid accumulator and said hypodermic needle, said first and second fluid medications being supplied from said fluid accumulator to said hypodermic needle by way of said fluid transfer port.

9. The fluid medication dispenser recited in claim 8, further comprising a needle hub, said needle hub carrying said hypodermic needle and having a fluid aperture formed therethrough for communicating with said hypodermic needle, said aperture through said needle hub communicating with said fluid transfer port through said housing so that said first and second fluid medications are supplied from said fluid accumulator to said hypodermic needle by way of said fluid transfer port and said fluid aperture.

10. The fluid medication dispenser recited in claim 1, further comprising means to move said hypodermic needle from a retracted position within said housing at which said hypodermic needle is shielded to an axially advanced position outwardly of said housing at which said hypodermic needle is exposed for administering an injection.

11. The fluid medication dispenser recited in claim 10, further comprising a guide track formed in and extending laterally across said housing, said hypodermic needle being moved through said guide track between said retracted position and said axially advanced position.

12. The fluid medication dispenser recited in claim 11, further comprising a needle control arm coupled to said hypodermic needle and riding through said guide track for moving said hypodermic needle between said retracted and axially advanced positions in response to a pushing force manually applied to said needle control arm; and
means by which to engage said needle control arm so as to releasably lock said needle control arm and thereby retain said hypodermic needle in each of said retracted and axially advanced positions.

13. The fluid medication dispenser recited in claim 12, further comprising a latch cover plate having a needle position control slot formed therethrough and first and second notches respectively located at opposite ends of said needle position control slot, said needle control arm being received in and sliding through said needle position control slot so as to be captured by one of said first and second notches at the opposite ends of said needle position control slot to prevent the displacement of said needle control arm through said guide track and thereby retain said hypodermic needle at one of said retracted and axially advanced positions.

14. The fluid medication dispenser recited in claim 13, wherein said latch cover plate is affixed to said housing so as to completely cover said guide track extending laterally across said housing.

15. Apparatus for administering an injection, comprising;
a body;
first and second fluid storage chambers extending within said body;
first and second fluids located within respective ones of said first and second fluid storage chambers;
a fluid accumulator extending within said body and communicating with said first and second fluid storage chambers;
first and second plungers moving through respective ones of said first and second fluid storage chambers to cause at least some of said first and second fluids to be delivered from said first and second fluid storage chambers to said fluid accumulator;
a hypodermic needle to be connected in fluid communication with said fluid accumulator for injecting said first and second fluids delivered to said fluid accumulator into living tissue;
an accumulator plunger moving through said fluid accumulator so as to cause said first and second fluids to be supplied from said fluid accumulator to said hypodermic needle; and
means by which move said hypodermic needle relative to said body between a retracted position inwardly of said body and an axially advanced position outwardly of said body at which to administer the injection.

16. The apparatus recited in claim 15, wherein said body is disk-shaped.

17. The apparatus recited in claim 15, further comprising first and second check valves located between respective ones of said first and second fluid storage chambers and said fluid accumulator to control the delivery of said first and second fluids from said first and second fluid storage chambers to said fluid accumulator.

18. The apparatus recited in claim 1, further comprising first and second plunger storage chambers extending through said body for removably receiving and storing respective ones of said first and second plungers, said first and second plungers being removed from said first and second plunger storage chambers to be positioned within and move through said first and second fluid storage chambers.

19. A fluid medication dispenser, comprising:
a housing having an interior and an exterior;
first and second fluid storage chambers extending within the interior of said housing;
first and second fluid medications located within respective ones of said first and second fluid storage chambers;
a fluid accumulator extending within the interior of said housing;
valve means by which to place said first and second fluid storage chambers in fluid communication with said fluid accumulator;
plunger means adapted to be positioned within and moved through said first and second fluid storage chambers to cause at least some of said first and second fluid medications to be delivered from said first and second fluid storage chambers to said fluid accumulator via said valve means;

a hypodermic needle located at a retracted and shielded position at the exterior of said housing so as to lie out of fluid communication with said fluid accumulator;

a fluid transfer port extending through said housing between the interior and the exterior thereof, said fluid transfer port communicating with said fluid accumulator;

means to slide said hypodermic needle in an axial direction along the exterior of said housing between said retracted and shielded position and an axially extended and exposed position so that said hypodermic needle is aligned with said fluid transfer port to communicate with said fluid accumulator; and means by which to cause said first and second fluid medications to be supplied from said fluid accumulator at the interior of said housing to said hypodermic needle at the exterior of said housing by way of said fluid transfer port extending therebetween so that an injection of said first and second fluid medications can be administered to living tissue with said hypodermic needle in the axially extended and exposed position.

20. The fluid medication dispenser recited in claim 19, further comprising a guide track formed in and extending across the exterior of said housing, said hypodermic needle sliding in said axial direction through said guide track between said retracted and shielded position and said axially extended and exposed position.

* * * * *